US011065264B2

(12) United States Patent
Levine et al.

(10) Patent No.: US 11,065,264 B2
(45) Date of Patent: Jul. 20, 2021

(54) METAL-OLSALAZINE COORDINATION POLYMERS FOR MEDICAL APPLICATIONS

(71) Applicant: THE REGENTS OF THE UNIVERSITY OF CALIFORNIA, Oakland, CA (US)

(72) Inventors: Dana J. Levine, Bonita, CA (US); Jeffrey R. Long, Oakland, CA (US); Miguel I. Gonzalez, Albany, CA (US)

(73) Assignee: THE REGENTS OF THE UNIVERSITY OF CALIFORNIA

( * ) Notice: Subject to any disclaimer, the term of this patent is extended or adjusted under 35 U.S.C. 154(b) by 0 days.

(21) Appl. No.: 16/209,480

(22) Filed: Dec. 4, 2018

(65) Prior Publication Data
US 2019/0192540 A1 Jun. 27, 2019

Related U.S. Application Data

(63) Continuation of application No. PCT/US2017/036453, filed on Jun. 7, 2017.
(Continued)

(51) Int. Cl.
*A61K 47/52* (2017.01)
*A61P 1/00* (2006.01)
(Continued)

(52) U.S. Cl.
CPC ............ *A61K 31/606* (2013.01); *A61K 47/18* (2013.01); *A61K 47/52* (2017.08); *A61K 47/6943* (2017.08); *A61P 1/00* (2018.01)

(58) Field of Classification Search
CPC ...... A61K 31/606; A61K 47/18; A61K 47/52; A61K 47/6943; A61P 1/00
See application file for complete search history.

(56) References Cited

FOREIGN PATENT DOCUMENTS

WO 2017214343 A1 12/2017

OTHER PUBLICATIONS

Meier et al. (Current treatment of ulcerative colitis World J Gastroenterol Jul. 21, 2011; 17(27): 3204-3212) (Year: 2011).*
(Continued)

*Primary Examiner* — Ernst V Arnold
(74) *Attorney, Agent, or Firm* — O'Banion & Ritchey LLP; John P. O'Banion

(57) ABSTRACT

Olsalazine ($H_4$olz), a prodrug of the anti-inflammatory 5-aminosalicylic acid, is used as a ligand to synthesize a suite of M($H_2$olz) and $M_2$(olz) materials, where M is a dication (e.g. Mg, Ca, Sr, Fe, Co, Ni, Cu, Zn). A family of metal olsalazine coordination polymers, coordination solids, and metal organic frameworks are described, which include 1-, 2-, and 3-dimensional structures. The materials resist degradation at acidic pH and release olsalazine preferentially at neutral pH. The mesoporous $M_2$(olz) frameworks exhibit high surface areas with hexagonal pore apertures that are approximately 27 Å in diameter and contain coordinatively unsaturated metal sites. Biologically active molecules containing a Lewis-basic functional group can be grafted directly to the open metal sites of the frameworks. Dissolution of the frameworks under physiological conditions releases olsalazine ($H_4$olz) and the grafted molecules so that multiple therapeutic components can be delivered together at different rates.

17 Claims, 7 Drawing Sheets

Related U.S. Application Data

(60) Provisional application No. 62/346,900, filed on Jun. 7, 2016.

(51) Int. Cl.
*A61K 31/606* (2006.01)
*A61K 47/69* (2017.01)
*A61K 47/18* (2017.01)

(56) References Cited

OTHER PUBLICATIONS

Levine et al. (JACS 2016;138:10143-10150; published Aug. 3, 2016). (Year: 2016).*
Donkor et al. Eur. J. Med. Chem. 2001;36:531-538). (Year: 2001).*
ISA/KR, Korean Intellectual Property Office (KIPO), International Search Report and Written Opinion dated Oct. 31, 2017, related PCT international application No. PCT/US2017/036453, pp. 1-16, claims searched, pp. 17-20.

Tang, Yun-Zhi et al., "Synthesis, characterization and crystal structures of two alkaline-earth metal complexes of olsalazine", Journal of Coordination Chemistry, 2008, 61:8, 1244-1252, published online Apr. 24, 2008.
Chen, Hai-Yan et al., "Two three-dimensional pillared metal-olsalazine complexes based on infinite rod-shaped secondary building units", Inorganica Chimica Acta 387 (2012) 283-288, published online Jan. 31, 2012.
Tang, Yun-Zhi et al., "Novel Three-Dimensional Anion-Type Eight-Coordinated Cd (II) Coordination Polymer with Binuclear Cadmium Building Units", American Chemical Society, Crystal Growth and Design, 2008, vol. 8, No. 6, pp. 1801-1803.
Xiao, Dong Rong et al., "Two unprecedented entangled metal-olsalazine complexes with coexistence of 2D→3D polycatenation and meso-helix", Eur. J. Inorg. Chem. 2011, 3656-3663.
Levine, Dana J. et al., "Olsalazine-based metal-organic frameworks as biocompatible platforms for HZ adsorption and drug delivery", J. Am. Chem. Soc. 2016, 138, 10143-10150, published Aug. 3, 2016.

* cited by examiner

METAL-OLSALAZINE COORDINATION POLYMERS FOR MEDICAL APPLICATIONS

CROSS-REFERENCE TO RELATED APPLICATIONS

This application claims priority to, and is a 35 U.S.C. § 111(a) continuation of, PCT international application number PCT/US2017/036453 filed on Jun. 7, 2017, incorporated herein by reference in its entirety, which claims priority to, and the benefit of, U.S. provisional patent application Ser. No. 62/346,900 filed on Jun. 7, 2016, incorporated herein by reference in its entirety. Priority is claimed to each of the foregoing applications.

The above-referenced PCT international application was published as PCT International Publication No. WO 2017/214343 A1 on Dec. 14, 2017, which publication is incorporated herein by reference in its entirety.

STATEMENT REGARDING FEDERALLY SPONSORED RESEARCH OR DEVELOPMENT

This invention was made with Government support under DE-SC0001015, awarded by the United States Department of Energy. The Government has certain rights in the invention.

INCORPORATION-BY-REFERENCE OF COMPUTER PROGRAM APPENDIX

Not Applicable

BACKGROUND

1. Technical Field

The technology of this disclosure pertains generally to metal-organic materials and fabrication methods, and more particularly compositions and methods for producing coordination polymers containing olsalazine for use in a variety of medical and pharmaceutical applications including drug formulation and delivery. In some embodiments, the coordination polymers can be used to modify the pharmacokinetics of olsalazine. In other embodiments, the porous materials can be used for encapsulation and delivery of therapeutics or imaging agents.

2. Background Discussion

Medicinal chemistry has produced an impressive array of small-molecule therapeutics for the treatment of disease. However, the utilization of many drug candidates is hindered by the presence of undesirable side effects or ineffective methods of delivery. Controlled release is one strategy that can improve the therapeutic efficacy of a drug while minimizing harmful side effects occurring in patients. Liposomes, micelles, polymer nano/microspheres, dendrimers, mesoporous silica, and other carriers have been established as useful vehicles for the delivery of therapeutic agents, and many such systems have already obtained FDA approval.

Another method to alter the release of a drug is to prepare salt formulations with different metal cations, hydration numbers, and structures. Drug formulation can be an effective tool for optimizing the therapeutic profile of an active pharmaceutical ingredient (API) because it modulates the properties and performance of an API while preserving its core structure. The administration of biologically active compounds as prodrugs can greatly enhance their performance by increasing their circulation time, absorption, and potency while protecting the active form of the molecules from degradation. For example, a prodrug can be designed to release its payload in response to specific stimuli such as enzymatic activity, pH, or redox potential.

Metals can be used to form various classes of compounds with bioactive molecules. In principle, any drug with a Lewis-basic functional group (e.g., —$O^-$, —$S^-$, —$NH_2$) can serve as a ligand to form complexes with biocompatible metals such as $Na^+$, $K^+$, $Mg^{2+}$, and $Ca^{2+}$. While simple salts are frequently used in drug formulation, drugs with two or more coordinating groups arranged appropriately can also allow the formation of extended networks, which can range in dimensionality from one-dimensional chains to three-dimensional structures. The nature of the resulting phase can also be influenced by the synthetic conditions used to make the materials. Such factors as solvent, temperature, metal source, stoichiometry, and reagent concentrations can be tuned to influence the reaction outcome, thereby allowing different materials to be obtained from the same metal and ligand combination. These materials can be amorphous or crystalline, forming coordination polymers or coordination solids, respectively. The three-dimensional structures can be dense or porous after removal of guest solvents, the latter of which are a class of materials known as metal-organic frameworks (MOFs).

Coordination solids and metal-organic frameworks have been increasingly investigated for potential applications in drug delivery due to their structural diversity, inherent modularity, and high drug-loading capacities. The potential biocompatibility or toxicity of the carrier or coordination solid components is an important consideration in the commercial applications of the materials. Indeed, there has been an increased focus on the development of low-toxicity metal-organic frameworks due to the necessary safety and environmental implications of their potential industrial applications.

For example, the delivery of a therapeutic dose of an agent may produce a significant level of degradation products from the carrier material that may be toxic. Components that are well-tolerated at low concentrations may present adverse effects at high concentrations. Degradation of the carrier in the body may produce a sizeable exposure to biologically reactive carrier components.

Accordingly, there is a need for the identification and production of materials that are biocompatible at an appropriate range of concentrations and allows control over the rate and location of release, the circulation time, the absorption, and the potency of active molecules that are protected from degradation.

BRIEF SUMMARY

The present technology provides olsalazine-based metal-organic coordination polymers as biocompatible platforms for delivery of drugs, bioactive molecules, macromolecules, and imaging agents. The therapeutic value of biologically active small molecules can be increased through coordination to biocompatible metals. In addition to altering the pharmacokinetic properties of a drug, the metal interaction can also be tuned to release the active drug in response to changes in the environment such as pH variations.

Olsalazine is a prodrug of the anti-inflammatory 5-aminosalicylic acid (5-ASA) that is used in the treatment of ulcerative colitis and other gastrointestinal diseases. Cleavage of olsalazine in the colon by bacteria results in two equivalents of the anti-inflammatory 5-ASA. Olsalazine has been shown to inhibit the development of colorectal cancer in patients, and it has also been proposed as a broad spectrum anticancer agent. Olsalazine is often taken daily in multi-gram doses, making it an effectively nontoxic ligand that can be useful in the design of new materials.

For patients with gastrointestinal diseases such as ulcerative colitis, olsalazine can cause significant side effects that arise from early release of large doses of the drug in the small intestine. To mitigate this, calcium-olsalazine coordination solids were synthesized that resist dissolution at low pH and gradually release olsalazine at neutral pH. The calcium materials also dissolved more slowly than the commercial sodium salt, providing improved olsalazine delivery to the colon while mitigating dose-dependent side effects.

Olsalazine ($H_4olz$) was used to form extended coordination solids, including one-dimensional chains ($Ca(H_2olz)$ $\cdot 4H_2O$), two-dimensional sheets ($Ca(H_2olz) \cdot 2H_2O$), and a flexible three-dimensional metal-organic framework ($Ca(H_2olz) \cdot 2DMF$) (DMF=N,N-dimethylformamide). The $Ca(H_2olz) \cdot 2DMF$ framework can be desolvated to produce a dense $Ca(H_2olz)$ phase upon treatment with aqueous acid. A new method for the rapid synthesis of a $Ca(H_2olz) \cdot 4H_2O$ one-dimensional phase, as well as a $Mg(H_2olz) \cdot 4H_2O$ one-dimensional chain phase, is also provided. A family of porous $M_2(olz)$ frameworks (M=Mg, Fe, Co, Ni, Zn) were also synthesized. The $M_2(olz)$ materials are also resistant to dissolution at low pH and disassemble under physiological conditions to release olsalazine. These materials are all highly crystalline and have been characterized by TGA, pXRD, and single crystal X-ray diffraction.

Calcium coordination solids were synthesized and evaluated for delivery of olsalazine ($H_4olz$). The $Ca(H_2olz) \cdot xH_2O$ (x=0, 2, 4) materials were each pressed into pellets and exposed to simulated gastrointestinal fluids to mimic the passage of a pill from the acidic stomach environment to the neutral pH of the intestines and colon. All three calcium materials released olsalazine more gradually when compared to the sodium salt control, which underwent rapid release under simulated intestinal conditions. These results suggest that the calcium coordination solids of olsalazine may provide advantages over the existing sodium formulations by minimizing side effects that arise from early release outside of the colon. The results also illustrate that the formulation of a drug within an extended coordination solid can serve to tune its solubility and performance.

In addition to the delivery of olsalazine alone, it is possible encapsulate a second drug in the large pores of the framework that provides a platform for delivery of multiple therapeutic components. The drug olsalazine ($H_4olz$) was employed as a ligand to synthesize a new series of porous metal-organic frameworks. The $M_2(olz)$ frameworks (M=Mg, Fe, Co, Ni, and Zn) exhibit high surface areas with large hexagonal pore apertures that are approximately 27 Å in diameter. Olsalazine exhibits the same coordinating functionality as the ligand 4,4'-dioxido-3,3'-biphenyldicarboxylate ($dobpdc^{4-}$), producing the MOF-74 architecture. Olsalazine is also slightly longer than $dobpdc^{4-}$, allowing it to accommodate larger guest molecules in the expanded pore of its corresponding frameworks.

Variable temperature $H_2$ adsorption isotherms revealed strong adsorption at the open metal sites, and in situ infrared spectroscopy experiments on $Mg_2(olz)$ and $Ni_2(olz)$ were used to determine site-specific $H_2$ binding enthalpies. In addition to binding of small gas molecules, the open metal sites of $Mg_2(olz)$ were also used to coordinate a number of bioactive compounds. This functionality was illustrated using the model drug phenethylamine (PEA), which was loaded into the pores of $Mg_2(olz)$ to generate $Mg_2(olz)(PEA)_2$, where both PEA and olsalazine can be subsequently released under physiological conditions.

The $Mg_2(olz)(PEA)_2$ material was also subjected to simulated biological conditions, and a controlled release of phenethylamine from the pores was observed, along with slower, concurrent dissolution of the framework. Under simulated physiological conditions, $Mg_2(olz)(PEA)_2$ disassembled to release PEA from the pores and olsalazine from the framework itself, demonstrating that multiple therapeutic components can be delivered together at different rates. The low toxicity, high surface areas, and coordinatively-unsaturated metal sites make these $M_2(olz)$ materials promising for a range of potential applications, including drug delivery in the treatment of gastrointestinal diseases.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only.

DETAILED DESCRIPTION

Referring more specifically to the drawings, for illustrative purposes, embodiments of methods for the synthesis of $M_2$(olz) frameworks and functionalized frameworks are generally shown. Several embodiments of the technology are described generally in the FIG. 1 FIG. 7 to illustrate the characteristics and functionality of the compositions and methods. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

The present technology provides a new suite of metal-olsalazine materials with the formulas M($H_2$olz).$xH_2O$ and $M_2$(olz) (x=0 to 10, M=dications such as Mg, Ca, Sr, Fe, Mn, Co, Ni, Cu and Zn).

Metal nodes and organic olsalazine linkers can be combined to form extended structures that have one-dimensional, two-dimensional, or three-dimensional connectivities. Such materials can be either crystalline or amorphous in nature. The $M_2$(olz) metal-organic frameworks exhibit very high surface areas and contain coordinatively-unsaturated metal sites that can be accessed by heating under dynamic vacuum.

Olsalazine is a prodrug of 5-aminosalicylic acid (5-ASA) that is used in the treatment of ulcerative colitis and also serves as a symmetric ligand for preparation of coordination solids. Bacterial azoreductases can selectively cleave the azo bond of olsalazine to give two equivalents of the anti-inflammatory 5-ASA locally. This is an effective strategy for the delivery of 5-ASA to the colon, since the concentration of gastrointestinal bacteria is highest in this region.

While olsalazine is an effective medication for the treatment of ulcerative colitis, high levels of the soluble drug in the small intestine can lead to severe side effects in patients with the disease. In addition, release of olsalazine in the small intestine may substantially diminish the available material reaching the target site of the colon. In order to modulate release, olsalazine can be transformed into various coordination solids including one-dimensional chains, two-dimensional sheets, and three-dimensional metal-organic frameworks with the present technology. These pH-responsive calcium-olsalazine materials, for example, minimize release of olsalazine under the acidic conditions of the stomach and small intestine while selectively releasing the bulk of the drug under the neutral conditions of the colon.

Figure 1:
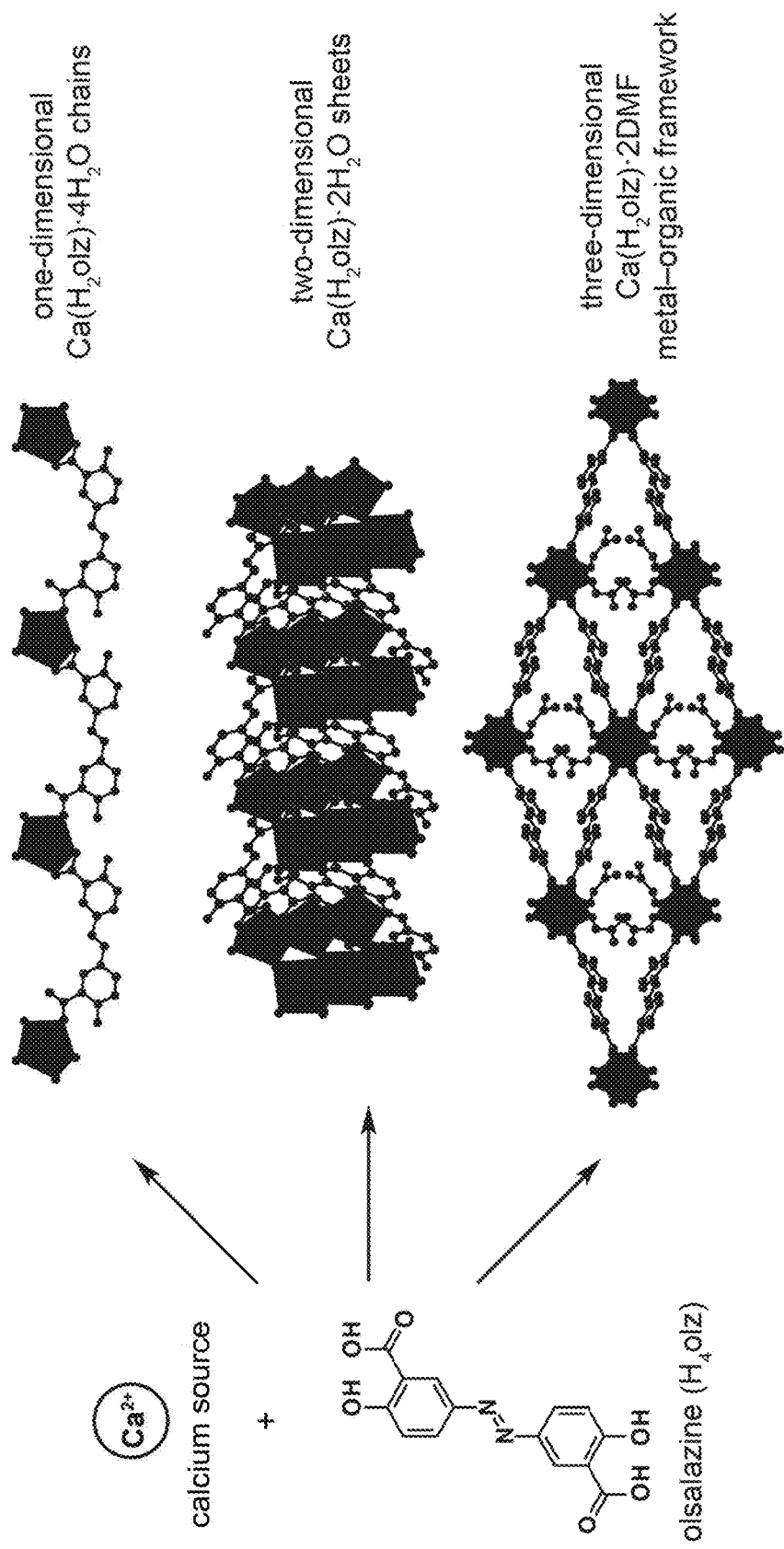
FIG. 1 shows portions of the crystal structures of $Ca(H_2olz) \cdot 4H_2O$ featuring one-dimensional chains, $Ca(H_2olz) \cdot 2H_2O$ containing two-dimensional sheets, and the three-dimensional metal-organic framework $Ca(H_2olz) \cdot 2DMF$ (DMF=N,N-dimethylformamide). These materials were synthesized using olsalazine acid ($H_4olz$) and a calcium(II) source according to one embodiment of the technology.

In one embodiment various biocompatible calcium coordination solids are formed with olsalazine as illustrated in FIG. 1. One-dimensional chains of Ca($H_2$olz).$4H_2O$ have been made through a fast synthesis with conditions that require only water as the solvent.

A new two-dimensional phase of Ca($H_2$olz).$2H_2O$ was also prepared, and its sheet-like structure was determined by single crystal X-ray diffraction.

A new three-dimensional framework of Ca($H_2$olz).2DMF may also be produced that exhibits remarkable flexibility upon immersion in different solvents such as methanol and aqueous acid. Upon exposure of this material to aqueous HCl, a dense Ca($H_2$olz) phase is produced with no solvent bound.

All three biocompatible calcium-olsalazine materials that were tested were more resistant to release of olsalazine under conditions simulating the small intestine as compared to the commercial sodium-olsalazine formulation. Furthermore, both the two-dimensional Ca($H_2$olz).$2H_2O$ and three-dimensional Ca($H_2$olz) phases have a higher percentage of the active pharmaceutical ingredient by weight (80% and 88%, respectively) than the commercially available disodium olsalazine (79%). Since patients are often required to take 2-3 gram doses of olsalazine per day, a higher efficiency product by weight would be another marked improvement over the current sodium salt formulation. Thus, these calcium-olsalazine coordination solids are promising materials for use in treatment of ulcerative colitis.

Accordingly, the $M_2$(olz) frameworks have potential therapeutic value, since they contain high quantities of the anti-inflammatory olsalazine that can be released under specified physiological conditions. This is especially true of $Mg_2$(olz), the least dense $M_2$(olz) framework, which exhibited the highest drug loading within any metal-organic framework made exclusively bioactive ligands. The observed disassembly of the drug-loaded frameworks into their original components is also advantageous for translation to clinical studies, since the safety and performance profiles will have been established previously for the constituent approved drugs.

Figure 5:
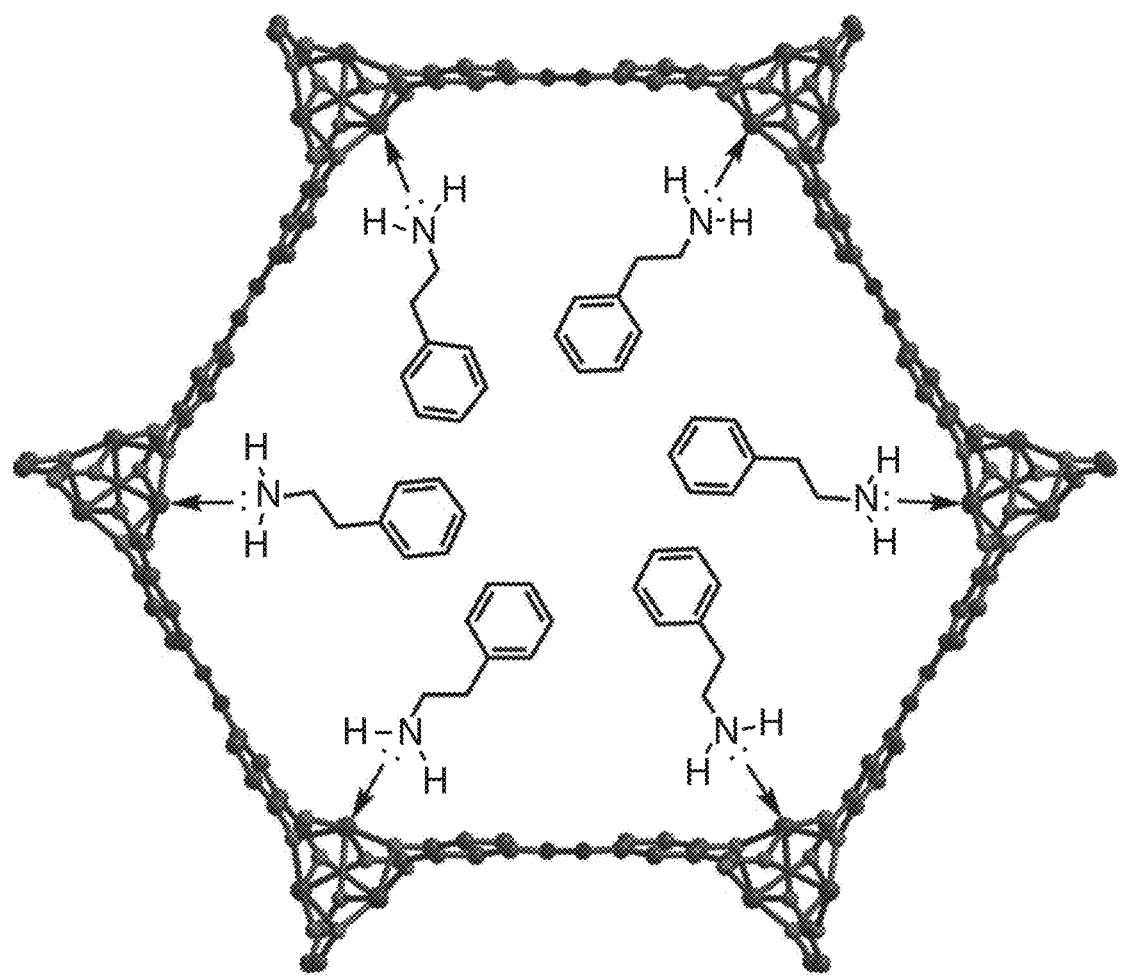
FIG. 5 is a schematic c-axis view of a $M_2(olz)$ framework pore functionalized with phenethylamine (PEA).

Turning now to FIG. 1 and FIG. 5, these mesoporous $M_2$(olz) framework materials may also serve as platforms for the simultaneous delivery of multiple therapeutic components. In addition to delivery of olsalazine, it is possible to encapsulate a second biologically active molecule in the large pores of the framework and successful release of both drugs under physiological conditions. This is illustrated in Example 4, where phenethylamine (PEA) can be loaded into the pores of $Mg_2$(olz) to generate $Mg_2$(olz)$(PEA)_2$, where both PEA and olsalazine can be subsequently released under physiological conditions.

Figure 4:
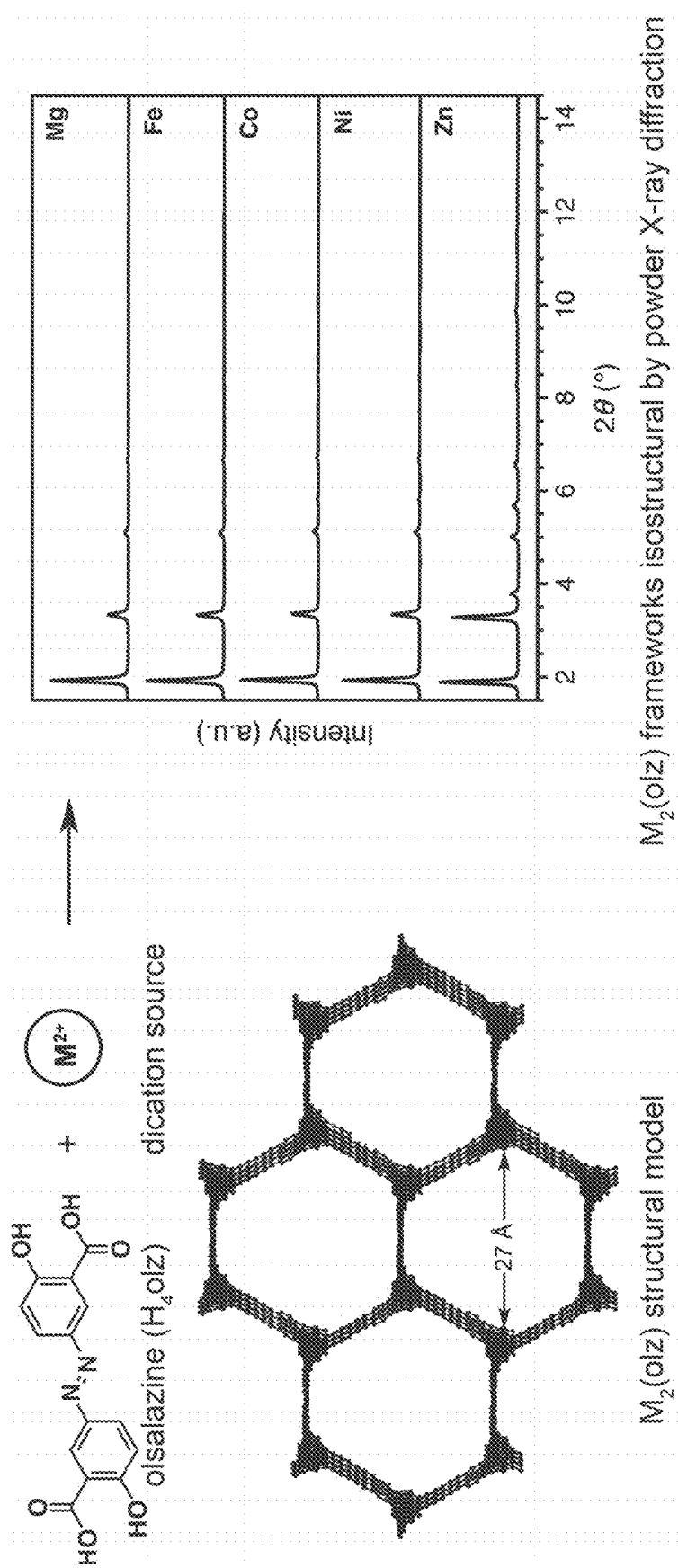
FIG. 4 is a structural model of the $M_2(olz)$ framework, where M=Mg, Fe, Co, Ni, and Zn. The frameworks are synthesized using olsalazine acid ($H_4olz$) and a dication source according to one embodiment of the technology. The powder X-ray diffraction patterns are shown for the activated $M_2(olz)$ frameworks (M=Mg, Fe, Co, Ni) and ethanol-solvated $Zn_2(olz)$.

This family of low-toxicity $M_2$(olz) frameworks has the potential to serve as a useful platform for diverse applications including gas storage and drug delivery. Upon activation, these materials exhibit high surface areas and contain pore apertures of approximately 27 Å with open metal sites as illustrated in FIG. 4 and FIG. 5.

The open metal sites of the framework can also be functionalized with selected to provide a platform for delivery of multiple therapeutic components. Through judicious choice of metal, it is possible to tailor the interaction between framework and drug to alter the strength of binding at the open metal site and tune the rate of release. For instance, the $Mg_2$(olz) and $Co_2$(olz) frameworks would be well suited for strong interactions with hard nitrogen and oxygen donors, while the $Zn_2$(olz) framework would be well matched for softer sulfur-based drugs loaded in solution. Additionally, the $Fe_2$(olz) framework could be oxidized to $[Fe_2(olz)]^{2+}$ as has been done for $Fe_2$(dobdc) and $Fe_2$(dobpdc), thereby producing a cationic framework capable of strong binding to anionic drugs. In some cases, it may also be beneficial to administer a precise ratio of metals in a drug formulation to serve as nutritional supplements or to address metal deficiencies in patients. Derivatives of $M_2$(dobdc) have been made with combinations of up to ten metals distributed throughout the framework in precise ratios, and a similar strategy could be pursued with $M_2$(olz) frameworks. This mixed-metal approach also provides a way to incorporate certain metal cations that are not easily prepared as a single-metal version of the framework (e.g. Ca, Sr).

An individual pore of the $M_2(olz)$ framework that has biologically active molecules grafted to the coordinatively-unsaturated metal sites of the framework is shown in FIG. 5. Generally, biologically active molecules containing a Lewis-basic functional group can be grafted directly to a metal center of the framework. Various functional groups, including amines, alkoxides, phenoxides, carboxylic acids and other anions can be grafted onto the open metal sites of the framework. The platform allows multiple therapeutic components to be delivered together at different rates.

For example, a variety of different primary and secondary phenethylamine derivatives of pharmaceutical importance are suitable for use with the platform, including: β-methylethylamine (TAAR 1 agonist); phentermine (appetite suppressant); phenzine (antidepressant); amphetamine (stimulant); levodopa (Parkinson's treatment); norepinephrine (hypotension treatment); and methyldopa (alpha-andrenergic antagonist).

Another example includes derivatives of N-methylphenethylamine (TAAR1 agonist) including: methamphetamine (stimulant); ephedrine (bronchodilator); pseudoephedrine (nasal decongestant); phenobarbital (anti-seizure medication); phenylephrine (decongestant); epinephrine (anaphylaxis); isoetarine (asthma) and salbutamol (COPD).

Accordingly, metal-organic coordination solids containing olsalazine can be used in a variety of medical and pharmaceutical applications including drug formulation and delivery. In some embodiments, the coordination solids can be used to modify the pharmacokinetics of olsalazine. In other embodiments, the porous frameworks can be used for encapsulation and delivery of other drugs, macromolecules, or imaging agents.

The technology described herein may be better understood with reference to the accompanying examples, which are intended for purposes of illustration only and should not be construed as in any sense limiting the scope of the technology described herein as defined in the claims appended hereto.

EXAMPLE 1

In order to demonstrate the operational principles of the framework and synthesis methods, olsalazine based metal organic frameworks were produced and processed.

Oral delivery of the anti-inflammatory drug 5-aminosalicylic acid (5-ASA) to the colon is problematic. When administered orally, 5-ASA is rapidly absorbed in the proximal small intestine, thereby diverting the drug away from the sites of inflammation in the colon and resulting in unnecessary systemic exposure. Thus, conventional oral administration of 5-ASA requires a formulation with either a pH-dependent enteric coating for delayed release or a semipermeable layer for sustained release.

While olsalazine disodium is effective for treatment of active ulcerative colitis and for maintenance of remission, as much as 35% of patients may experience diarrhea as a side effect, causing over 10% of patients to discontinue treatment. This side effect has been attributed to increased anion secretion in the ileum, as well as inhibition of NaCl absorption in the small intestine. These effects are dose-dependent and have also been observed with other azo-linked prodrugs of 5-ASA. Such side effects may be diminished with a formulation that minimizes olsalazine release throughout the upper gastrointestinal tract.

Calcium coordination solids were synthesized as shown in FIG. 1 and later evaluated for delivery of olsalazine ($H_4$olz). FIG. 1 shows portions of the crystal structures of Ca($H_2$olz).4$H_2$O featuring one-dimensional chains, Ca($H_2$olz).2$H_2$O containing two-dimensional sheets, and the three-dimensional metal-organic framework Ca($H_2$olz).2DMF (DMF=N,N-dimethylformamide). These materials were synthesized using olsalazine acid ($H_4$olz) and a calcium(II) source. Calcium-based solids were selected because they are known to produce a variety of architectures with dicarboxylate ligands. In addition, the $Ca^{2+}$ component itself may provide therapeutic benefits for patients with ulcerative colitis. Calcium coordination solids that form one-, two-, and three-dimensional structures with olsalazine acid ($H_4$olz) were prepared and investigated as alternatives to the existing olsalazine disodium formulation.

Calcium coordination solids were synthesized and evaluated for delivery of olsalazine ($H_4$olz). Calcium-based solids were selected because they are known to produce a variety of architectures with dicarboxylate ligands. In addition, the $Ca^{2+}$ component itself may provide therapeutic benefits for patients with ulcerative colitis. Calcium coordination solids that form one-, two-, and three-dimensional structures with olsalazine acid ($H_4$olz) were prepared and investigated as alternatives to the existing olsalazine disodium formulation.

Synthesis of the structure of Ca($H_2$olz).4$H_2$O featuring one-dimensional chains was performed with a rapid synthesis from Ca($NO_3$)$_2$.4$H_2$O and olsalazine that requires only water as the solvent and a reaction time of a few hours. The structure consisted of pentagonal bipyramidal $Ca^{2+}$ ions that are each coordinated to four water molecules and three carboxylate oxygen atoms from two different olsalazine molecules, where one carboxylate coordinates in a monodentate fashion and the other in a bidentate fashion. Each olsalazine bridges two $Ca^{2+}$ ions to produce the one-dimensional chains.

Synthesis of Ca($H_2$olz).4$H_2$O one-dimensional chains was performed by first dissolving the metal salt Ca(NO$_3$)$_3$.4$H_2$O (112 mg, 0.473 mmol) in 5 mL of water and separately dissolving olsalazine acid (68.0 mg, 0.225 mmol) in 10 mL water with addition of NaOH (18.0 mg, 0.450 mmol). The olsalazine solution was allowed to reach 90° C. and the metal salt solution was added under heavy stirring. The mixed solution was heated and left stirring overnight. The dark orange powder was collected on a funnel and dried to obtain the microcrystalline powder.

In an alternative synthesis, Ca(OAc)$_2$.2$H_2$O (27.7 mg, 0.160 mmol) was dissolved in 1 mL of water and olsalazine acid (22.7 mg, 0.0750 mmol) was suspended in 4 mL of water with sonication. The combined solutions were then sonicated together and left to heat at 90° C. to produce yellow or red crystals depending on size. A shorter sonication time (1 min) correlated with larger crystals, while longer sonication times (>5 min) produced a more uniform distribution of crystals by size. An analogous method was used to prepare one-dimensional chains of Mg($H_2$olz).4$H_2$O starting from Mg(OAc)$_2$.4$H_2$O.

A new two-dimensional phase, Ca($H_2$olz).2$H_2$O was obtained through reaction conditions similar to those developed for the one-dimensional chains. While sonication or stirring of the reaction mixture at elevated temperature tends to favor the one-dimensional phase, leaving the reaction undisturbed tends to favor the two-dimensional phase. This behavior suggested a delicate balance in the reaction kinetics and thermodynamics that govern the formation of one phase over the other. The sheets within this crystal structure are comprised of pentagonal bipyramidal $Ca^{2+}$ atoms, which are each coordinated to two water molecules in a cis geometry and five carboxylate oxygen atoms from olsalazine.

For the synthesis of Ca($H_2$olz).2$H_2$O in two-dimensional sheets, the metal salt Ca(NO$_3$)$_2$.4$H_2$O (74.4 mg, 0.315 mmol) was dissolved in 3 ml of water, and olsalazine acid (45.3 mg, 0.150 mmol) was dissolved in 1 mL of water with NaOH (12.0 mg, 0.300 mmol). The ligand solution was added to the metal solution at room temperature, producing an orange precipitate upon mixing. The vial was then heated undisturbed at 90° C. for 12 h to produce the product as a microcrystalline powder.

In an alternative synthesis, Ca(NO$_3$)$_2$.4$H_2$O (18.6 mg, 0.0788 mmol, 2.1 equiv.) and Na$_2$(H$_2$olz) (13.0 mg, 0.0375 mmol) were dissolved in 0.5 mL and 2 mL of water, respectively. The solutions were combined, producing a transient yellow precipitate that dissolved upon heating at 90° C. The vial was left to heat undisturbed at 90° C. to produce yellow crystals. Longer reaction times can be used to produce larger crystals. Note that sonication or stirring of the reaction mixtures described may favor the one-dimensional phase, so it is important to minimize agitation to promote formation of the two-dimensional phase under these conditions.

Reaction of Ca(NO$_3$)$_2$.4$H_2$O and olsalazine in a mixture of DMF and ethanol under solvothermal conditions yielded single crystals of the three-dimensional metal-organic framework Ca(H$_2$olz).2DMF (3.DMF). In this structure, the Ca$^{2+}$ ions exhibit an octahedral coordination environment with two DMF molecules bound in the axial positions and carboxylate oxygen atoms from four different olsalazine ligands bound in the equatorial positions. The framework 3.DMF demonstrated remarkable flexibility, undergoing significant structural changes in the presence of different solvents. Similar behavior has been observed for other calcium frameworks with dicarboxylate ligands.

Figure 2:
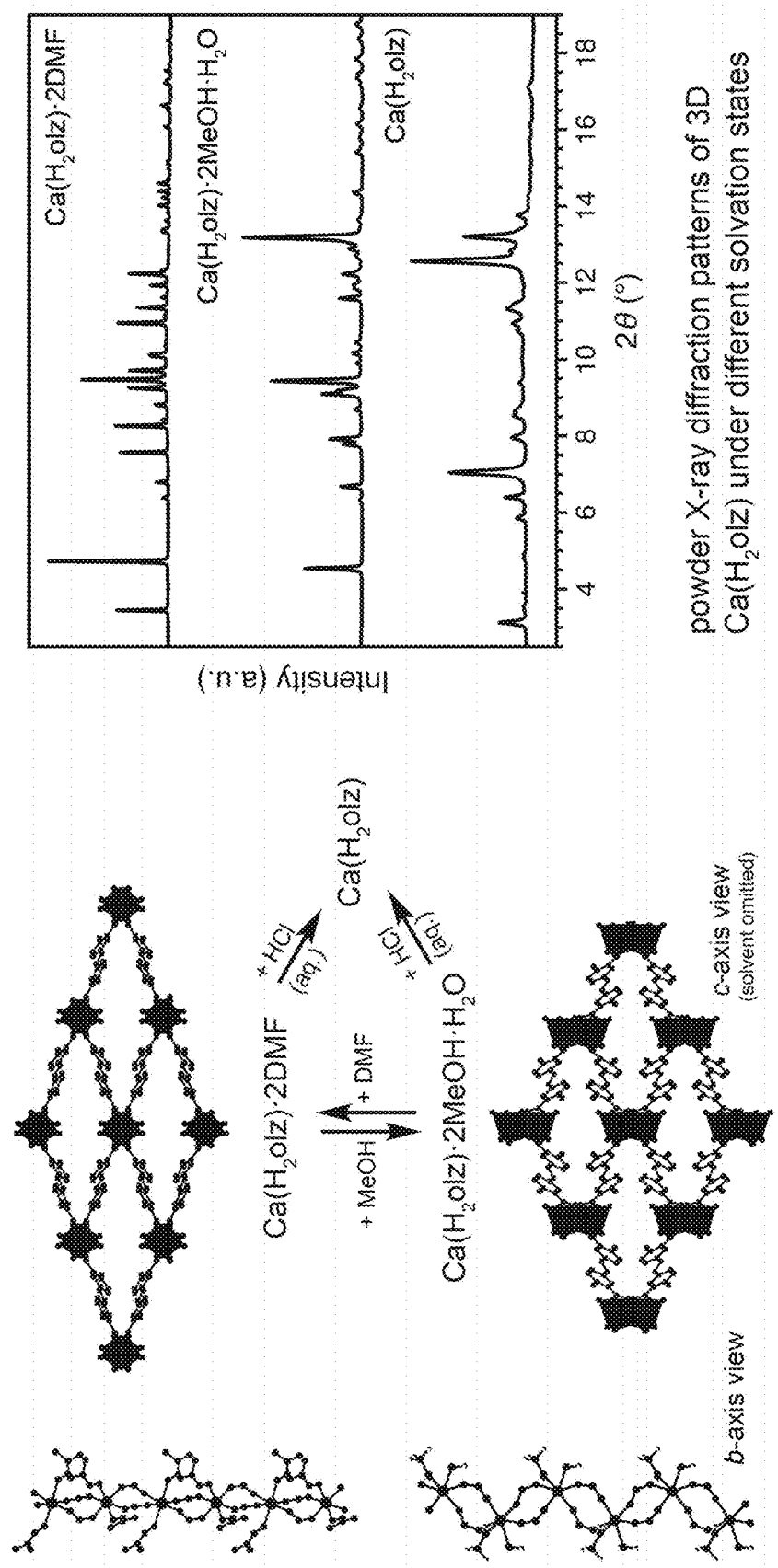
FIG. 2 illustrates the flexibility of the three-dimensional $Ca(H_2olz)$ material when exposed to different solvent conditions. A collapsed phase of $Ca(H_2olz)$ is obtained after exposure of either the DMF or methanol phases to aqueous HCl, producing a dense 90 wt % formulation of olsalazine with a characteristic X-ray powder diffraction pattern.

FIG. 2 illustrates the flexibility of the three-dimensional Ca(H$_2$olz) material when exposed to different solvent conditions. A collapsed phase of Ca(H$_2$olz) is obtained after exposure of either the DMF or methanol phases to aqueous HCl, producing a dense 90 wt % formulation of olsalazine with a characteristic X-ray powder diffraction pattern.

Exposure of 3.DMF to wet methanol produces a new phase with the formula Ca(H$_2$olz).2MeOH.H$_2$O (3.MeOH), whose structure was determined by powder X-ray diffraction. Immersion of either 3.DMF or 3.MeOH in 100-mM aqueous HCl irreversibly generates a third phase, likely with an accompanying change in ligand coordination mode. While the powder pattern of this phase could not be indexed to determine the structure, thermogravimetric analysis showed a single mass loss event at approximately 250° C. corresponding to decomposition. In conjunction with elemental analysis, this result corroborates a dense phase with the formula Ca(H$_2$olz) in which no solvent is present.

For the synthesis of Ca(H$_2$olz).2DMF three-dimensional framework, the metal salt Ca(NO$_3$)$_2$.4$H_2$O (117 mg, 0.495 mmol) was dissolved in 12 mL of EtOH and olsalazine acid (136 mg, 0.450 mmol) was dissolved in 18 mL of DMF. These solutions were combined in a jar and separated into six 10-mL aliquots in 20-mL scintillation vials. The vials were then heated in a dry bath at 120° C. for 1 d. The solvent mixture was decanted to isolate the product as dark orange needles by filtration (124 mg, 56.5% yield). Note that washing with DMF can partially dissolve the crystals and should be minimized. A bulk microcrystalline powder can also be prepared by stirring the reaction mixture described above at 120° C.

EXAMPLE 2

To evaluate the potential utility of Ca(H$_2$olz).x$H_2$O coordination solids in the treatment of ulcerative colitis (x=4, 2, and 0 for 1D, 2D, and 3D materials, respectively), each material was tested for drug release in comparison with Na$_2$(H$_2$olz), which is the salt used in the commercial formulation (available as Dipentum®). Each material was pressed into a pellet and exposed to solutions that mimic the pH of the stomach, small intestine, and colon. The pH and composition of the release medium was changed by addition of buffers in accordance to the expected transit times of a pill through the gastrointestinal tract: the first two hours were held at pH 1.1, the next two hours at pH 6.0, and the final six hours at pH 7.3. The vessels containing the pellet in release media were shaken at 60 rpm at 37° C. to simulate the motion and temperature of the body.

Sample pellets were prepared from pure material without binders or other agents typically used for pill preparation in the pharmaceutical industry. This was done in order to probe the properties of each material without influence from any excipients. Due to this method of preparation, however, pellets were susceptible to disintegration, which can accelerate the observed dissolution rates. The calcium-olsalazine chains (1) and sheets (2), as well as the sodium-olsalazine material, partially disintegrated once in contact with the solution. The variability in pellet integrity likely contributed to the large observed standard deviation. Notably, the Ca(H$_2$olz) framework (3) consistently resisted disintegration throughout the release experiments.

Figure 3:
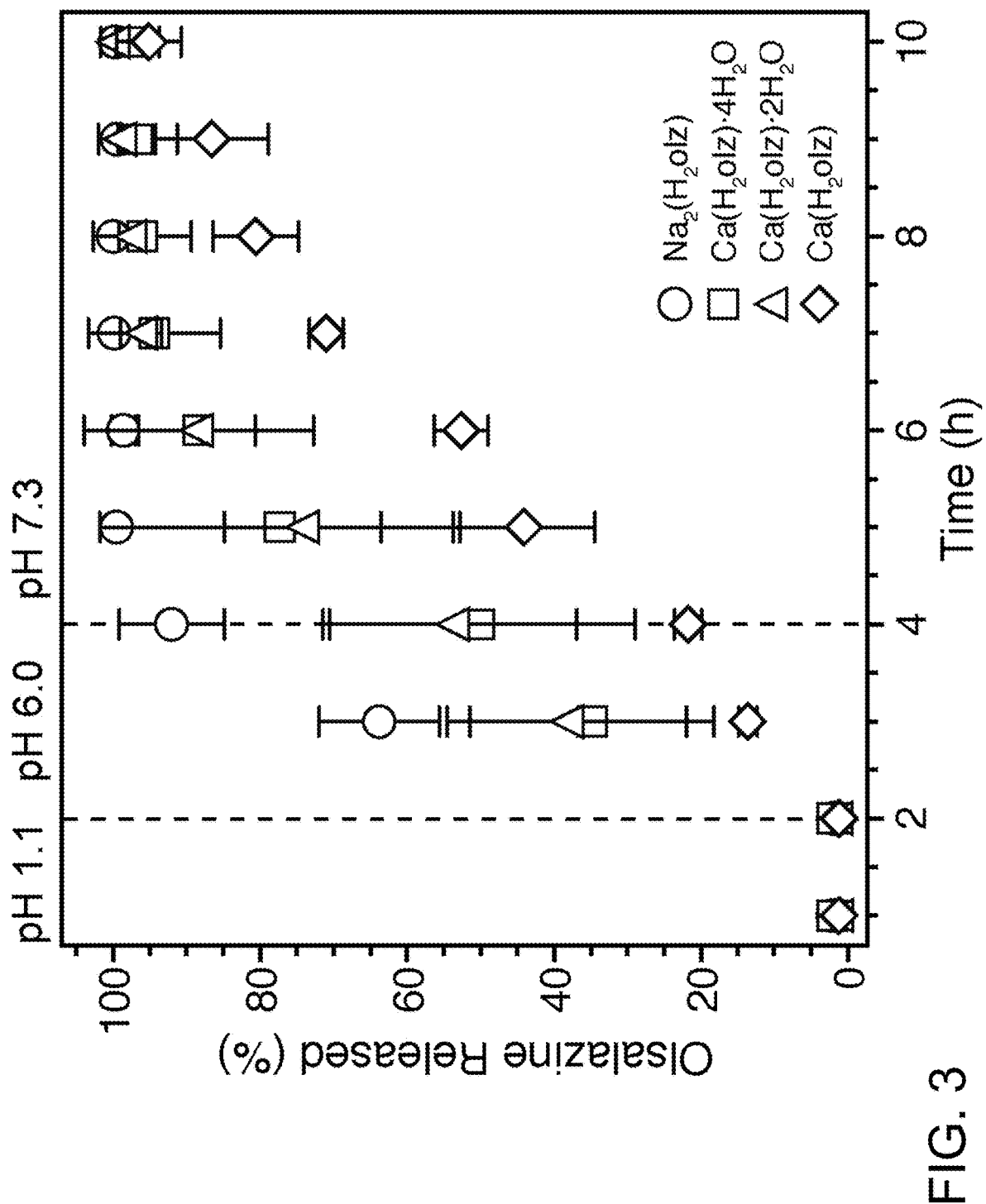
FIG. 3 is a graph of the release of olsalazine from $Na_2(H_2olz)$ (circles) and $Ca(H_2olz) \cdot xH_2O$ materials under simulated gastrointestinal conditions (x=4, 2, 0, denoted by squares, triangles, and diamonds, respectively). Error bars represent standard deviation across three independent data sets, where the quantity of olsalazine in solution was measured spectroscopically ($\lambda$=360 nm). The release media were changed throughout the study to emulate the typical pH and transit times of a pill passing through the stomach (pH 1.1, 2 h), small intestine (pH 6.0, 2 h), and colon (pH 7.3, 6 h).

FIG. 3 is a graph of the release of olsalazine from Na$_2$(H$_2$olz) (circles) and Ca(H$_2$olz).x$H_2$O materials under simulated gastrointestinal conditions (x=4, 2, 0, denoted by squares, triangles, and diamonds, respectively). Error bars represent standard deviation across three independent data sets, where the quantity of olsalazine in solution was measured spectroscopically ($\lambda$=360 nm). The release media were changed throughout the study to emulate the typical pH and transit times of a pill passing through the stomach (pH 1.1, 2 h), small intestine (pH 6.0, 2 h), and colon (pH 7.3, 6 h).

All three of the Ca(H$_2$olz) materials outperformed Na$_2$(H$_2$olz) by providing slower release of olsalazine in the simulated gastrointestinal environment. While all materials resisted dissolution at pH 1.1, the Na$_2$(H$_2$olz) dissolved more rapidly than the Ca(H$_2$olz) materials at pH 6.0 and above. The difference in dissolution rates is particularly clear when comparing the amount of drug released at the four-hour time point, where over 90% of the olsalazine had been released from Na$_2$(H$_2$olz) while about 50% had been released from the Ca(H$_2$olz).4H$_2$O chains and the Ca(H$_2$olz).2H$_2$O sheets. Notably, the dense Ca(H$_2$olz) framework (3) had released less than 25% of the drug at the same point. While these differences in solubility rates can be partly attributed to differences in pellet integrity, the improved resistance of the Ca(H$_2$olz) materials to dissolution may nevertheless aid in preserving olsalazine as a solid throughout the upper gastrointestinal tract.

Multiple properties of the sodium- and calcium-olsalazine materials may contribute to the observed differences in drug release. For example, the differences in solubility are consistent with the expected trends for hard carboxylate donors with Na$^+$ versus Ca$^{2+}$. Both the local and extended structure of the coordination solids may also play a role in governing the dissolution rates, since the three-dimensional material exhibits a distinct release profile compared to the other calcium-olsalazine materials. Since the materials resisted disintegration to different degrees, however, it is difficult to deconvolute the specific effects of crystal structure with that of other macroscopic or mechanical properties of the materials when compressed into a pellet without excipients.

Historically, sodium has been used far more frequently than other metal cations in drug formulation, largely due to its tendency to increase the solubility of an API over its free acid form. It was demonstrated that calcium can be used to synthesize new solid-state architectures that may further optimize the performance of an existing API by refining its release rates and solubility under physiological conditions. The slow-release properties of the $Ca(H_2olz).xH_2O$ (x=0, 2, 4) coordination solids provides advantages over the commercial $Na_2(H_2olz)$ formulation by potentially reducing the side effects associated with soluble olsalazine in the small intestine.

EXAMPLE 3

Porous metal-organic frameworks of $M_2(olz)$, where M=Mg, Fe, Co, Ni, and Zn, were synthesized and evaluated. Upon activation, these materials exhibit high surface areas and contain pore apertures of approximately 27 Å. Gas sorption measurements of the desolvated $M_2(olz)$ materials were also performed. Strong $H_2$ adsorption was observed by gas sorption studies and in situ infrared spectroscopy, confirming the presence of open metal sites.

The $M_2(olz)$ frameworks were synthesized, and through optimization of reaction conditions such as solvent composition and temperature, it was possible to isolate microcrystalline powder samples for all of the investigated metals. Powder X-ray diffraction revealed that the solvated and activated $M_2(olz)$ frameworks are all isostructural.

FIG. 4 provides a structural model of the $M_2(olz)$ framework, where M=Mg, Fe, Co, Ni, and Zn. The frameworks were synthesized using olsalazine acid ($H_4olz$) and a dication source. The powder X-ray diffraction patterns are shown for the activated $M_2(olz)$ frameworks (M=Mg, Fe, Co, Ni) and ethanol-solvated $Zn_2(olz)$, and the Langmuir surface areas are provided in $m^2/g$.

Synthesis of $Mg_2(olz)$: The metal salt $Mg(NO_3)_2.6H_2O$ (242 mg, 0.945 mmol) was dissolved in 12 mL of ethanol, and $H_4olz$ (136 mg, 0.450 mmol) was dissolved separately in 18 mL of N,N-dimethylformamide (DMF). These solutions were combined in a 50-mL Pyrex glass jar, sealed, and heated in an isothermal oven at 120° C. for 1 day. The reaction mixture was subsequently decanted, and the damp yellow solid was washed with successive aliquots of DMF (3×30 mL) at 80° C. followed by aliquots of methanol (3×30 mL) at 60° C. The slurry was then transferred to a tared analysis tube, and excess solvent was removed via cannula. The framework was activated for 12 h at 180° C. under a flow of argon and then placed under vacuum on an ASAP 2420 instrument at the same temperature. Activated yield: 125 mg (80% based on ligand).

Synthesis of $Fe_2(olz)$: In a nitrogen-filled glove box, a 20-mL vial was charged with $H_4olz$ (30 mg, 0.10 mmol) and $FeCl_2$ (30 mg, 0.24 mmol). Methanol (5 mL) and DMF (5 mL) were added, and the vial was sealed with a PTFE-lined cap and shaken until a homogeneous solution formed. The vial was placed on a dry bath preheated to 100° C. and left at this temperature, without stirring, for 16 h. The dark red/brown precipitate that had formed after this time was collected by filtration and washed with a small amount of methanol. The solid was washed with successive aliquots of DMF (3×15 mL) at 100° C. followed by aliquots of methanol (5×15 mL) at 60° C. After the final wash, the dark red/brown solid was collected by filtration and dried under reduced pressure. In a glove box, the methanol-solvated $Fe_2(olz)$ was placed in a tared glass ASAP tube equipped with a Transeal. The tube was removed from the box and heated under vacuum to 120° C. at a rate of 0.2° C./min to give $Fe_2(olz)$. Synthesis of other air-sensitive $M_2(olz)$ derivatives such as $Mn_2(olz)$ is accomplished by an analogous method.

Synthesis of $Co_2(olz)$: The metal salt $Co(NO_3)_2.6H_2O$ (72.8 mg, 0.250 mmol) was dissolved in 3.3 mL of ethanol and 3.3 mL of water, and $H_4olz$ (30.2 mg, 0.100 mmol) was dissolved separately in 3.3 mL of N,N-dimethylacetamide (DMA). The solutions were combined in a 10-mL Pyrex glass jar, sealed, and heated in an isothermal oven at 100° C. for 1 day. The reaction mixture was decanted, and the orange powder was washed with successive aliquots of DMF (3×10 mL) at 80° C. and methanol (3×10 mL) at 60° C. The slurry was then transferred to a tared analysis tube where excess solvent was removed via cannula. The framework was activated for 12 h at 180° C. under an argon flow and then placed under vacuum at the same temperature on an ASAP 2420 instrument.

Synthesis of $Ni_2(olz)$: The metal salt $Ni(NO_3)_2.6H_2O$ (218 mg, 0.750 mmol) was dissolved in 10 mL of ethanol and 10 mL of $H_2O$, and $H_4olz$ (90.7 mg, 0.300 mmol) was dissolved separately in 10 mL of DEF. These solutions were combined and then distributed into three 20-mL glass scintillation vials, sealed with a PTFE-lined cap, and heated in a dry bath at 100° C. for 1 day. The reaction mixtures were then combined and the solvent was decanted. The resulting orange solid was washed with successive aliquots of DMF (3×20 mL) at 80° C. followed by aliquots of methanol (3×20 mL) at 60° C. The slurry was then transferred to a tared analysis tube where excess solvent was removed via cannula. The framework was activated for 12 h at 180° C. under a flow of argon and then placed under vacuum at the same temperature on an ASAP 2420 instrument.

Synthesis of $Cu_2(olz)$: The metal salt $Cu(NO_3)_2.5H_2O$ is dissolved in 1 mL of ethanol and 1 mL of $H_2O$, and $H_4olz$ is dissolved separately in 1 mL of DEF. These solutions are combined, sealed in a scintillation vial with a PTFE-lined cap, and heated in a dry bath at 100° C. for 1 day. The resulting solid is washed with successive aliquots of DMF (3×20 mL) at 80° C. followed by aliquots of methanol (3×20 mL) at 60° C. The slurry is then transferred to a tared analysis tube where excess solvent is removed via cannula. The framework is activated for 12 h at 180° C. under a flow of argon and then placed under vacuum at the same temperature on an ASAP 2420 instrument.

Synthesis of $Zn_2(olz)$: The metal salt $Zn(NO_3)_2.6H_2O$ (298 mg, 1.00 mmol) was dissolved in 20 mL of ethanol, and $H_4olz$ (121 mg, 0.400 mmol) was dissolved separately in 20 mL of DMA. These solutions were combined and then distributed into four 20-mL glass scintillation vials, sealed with a PTFE-lined cap, and heated in dry bath at 100° C. for 1 day. The reaction mixtures were then combined and the solvent was decanted. The resulting yellow solid was washed with successive aliquots of DMF (3×20 mL) at 80° C. followed by aliquots of methanol (3×20 mL) at 60° C. The resulting methanol slurry was then transferred to a tared analysis tube where excess solvent was removed. The framework was activated under argon flow at 100° C. for 12 h and then under vacuum at the same temperature on an ASAP 2420 instrument.

The as-synthesized $M_2(olz)$ frameworks were activated by performing successive solvent exchanges with DMF and methanol, followed by heating under argon and vacuum to remove residual or coordinated solvent. Surface areas of the desolvated $M_2(olz)$ frameworks were then determined from $N_2$ adsorption measurements performed at 77 K. With the exception of $Zn_2(olz)$, which appeared to lose crystallinity upon activation, the $M_2(olz)$ frameworks exhibited high surface areas that are consistent with the expanded linker size. The Langmuir surface areas were the highest reported for any framework with a bioactive molecule as the sole linker.

EXAMPLE 4

The high biocompatibility and large pore dimensions of the $M_2(olz)$ frameworks make them good candidates for drug delivery applications. Given the low atomic weight of Mg and its role as an essential metal in the human diet, $Mg_2(olz)$ was selected for the initial drug release studies. Pellets of the $Mg_2(olz)$ framework were and exposed to simulated physiological conditions (37° C. PBS solution at pH 7.4 with bidimensional stirring at 60 rpm) to evaluate framework disassembly and olsalazine release. Aliquots were collected from the buffered solution at different time points, and the appearance of olsalazine was tracked by measuring its characteristic absorbance at 360 nm. The resulting degradation profile of $Mg_2(olz)$ showed a gradual release of olsalazine as the framework disassembled into its constituent parts. This release behavior, coupled with the high olsalazine composition, make $Mg_2(olz)$ a good candidate for delivery of the anti-inflammatory therapeutic. The other $M_2(olz)$ frameworks exhibited similar dissolution behavior under simulated physiological conditions.

To demonstrate the utility of the porous $M_2(olz)$ frameworks as platforms for co-delivery of a second active molecule with olsalazine, phenethylamine (PEA) was selected as a model drug for loading. PEA was selected because derivatives of this molecule form a large class of bioactive compounds with diverse pharmacological properties (e.g., stimulants, appetite suppressants, antidepressants, and anti-Parkinsonian agents etc.). Due to the extensive metabolism and addictive nature of some of these compounds, there is a need for controlled release formulations that reduce dramatic fluctuations in drug concentrations while maintaining adequate therapeutic levels over time. In this way, a controlled release dosage form may improve performance of the drug while reducing the likelihood of side effects and abuse.

By taking advantage of the coordinatively-unsaturated metal sites and large pore apertures of the $M_2(olz)$ frameworks, it is possible to graft drugs or other biologically active molecules containing a Lewis-basic functional group directly to the metal of the framework. Previous studies have demonstrated grafting of various functional groups, including amines, alkoxides, phenoxides, carboxylic acids and other anions onto the open metal sites of the smaller MOF-74 analogs. Biologically active molecules possessing these functional groups or drugs with a metal-coordinating moiety can be similarly coordinated to the open metal sites of the $M_2(olz)$ frameworks.

To illustrate this application, the $Mg_2(olz)(PEA)_2$ material was prepared for evaluation. PEA was incorporated into $Mg_2(olz)$ by soaking the framework in a 20% solution of the drug in $CH_2Cl_2$ under an inert $N_2$ atmosphere. After 24 h, the resulting material was washed and dried, and the stoichiometry was confirmed by $^1H$ NMR spectroscopy as two PEA per olsalazine, or one PEA per $Mg^{2+}$ ion. A structural model for $Mg_2(olz)(PEA)_2$ is shown schematically in FIG. 5, where the amine of PEA is coordinated to the $Mg^{2+}$ open metal sites in the observed 1:1 stoichiometry. FIG. 5 is a schematic c-axis view of a $M_2(olz)$ framework pore functionalized with phenethylamine (PEA). The secondary amine N-methylphenethylamine was also shown to bind to $Mg_2(olz)$ in the expected stoichiometry of one amine per metal, indicating that $Mg_2(olz)$ is a versatile platform that can accommodate a variety of phenethylamine derivatives.

In order to simulate physiological conditions for drug release, the $Mg_2(olz)(PEA)_2$ material was pressed into 4-mm pellets, which were immersed in PBS with shaking at 37° C. Aliquots were taken at regular time points until the framework was fully dissolved, and release of both PEA and olsalazine was quantified by reversed-phase HPLC as seen in FIG. 6.

Figure 6:
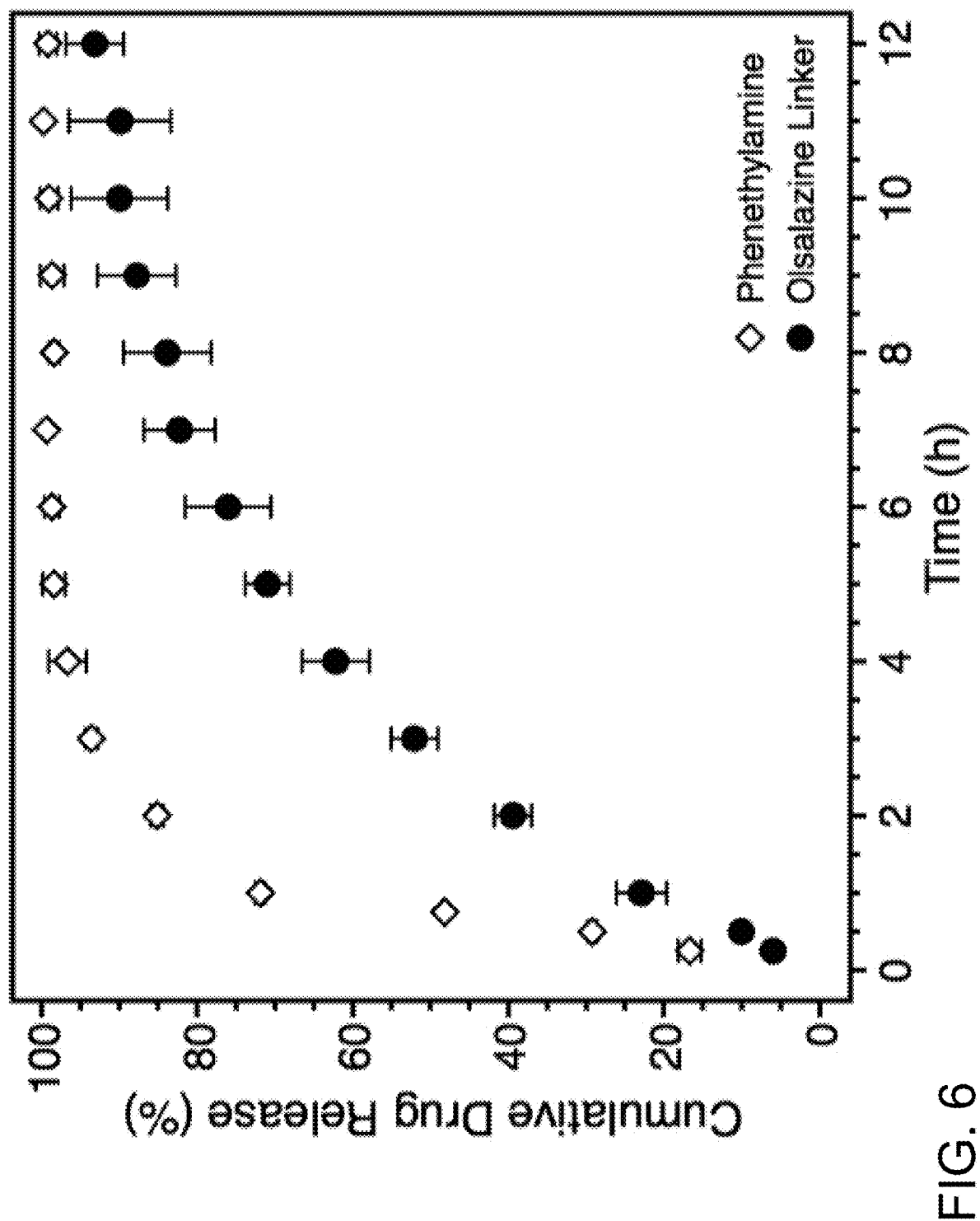
FIG. 6 is a graph of the release of phenethylamine and olsalazine from $Mg_2(olz)(PEA)_2$ under simulated biological conditions (PBS, pH=7.4, 37° C.). Error bars represent standard deviation for release from triplicate pellet samples.

FIG. 6 is a graph of the release of phenethylamine and olsalazine from $Mg_2(olz)(PEA)_2$ under simulated biological conditions (PBS, pH=7.4, 37° C.). Error bars represent standard deviation for release from triplicate pellet samples.

Based on the observed cumulative release shown in the graph of FIG. 6, the PEA is released more rapidly than the olsalazine linker. For example, approximately 95% of PEA was released compared to 50% of the olsalazine after 3 hours. This suggested that PEA may be displaced as water diffuses into the one-dimensional channels prior to the dissolution of the framework itself, resulting in multi-rate drug release.

In $Mg_2(olz)(PEA)_2$, over 90% of the material by weight consists of a therapeutic organic molecule, with PEA and olsalazine accounting for 41% and 51% of the weight, respectively. Such high concentrations of active pharmaceutical ingredients are desirable as they can reduce the size of the administered dose and minimize the need for other components that may produce side effects in some patients. The disassembly of the loaded framework into components that have well-established pharmacological and safety profiles in humans is also a beneficial feature that can greatly expedite the translation of any promising $M_2(olz)$ materials into a clinical setting.

EXAMPLE 5

Figure 7:
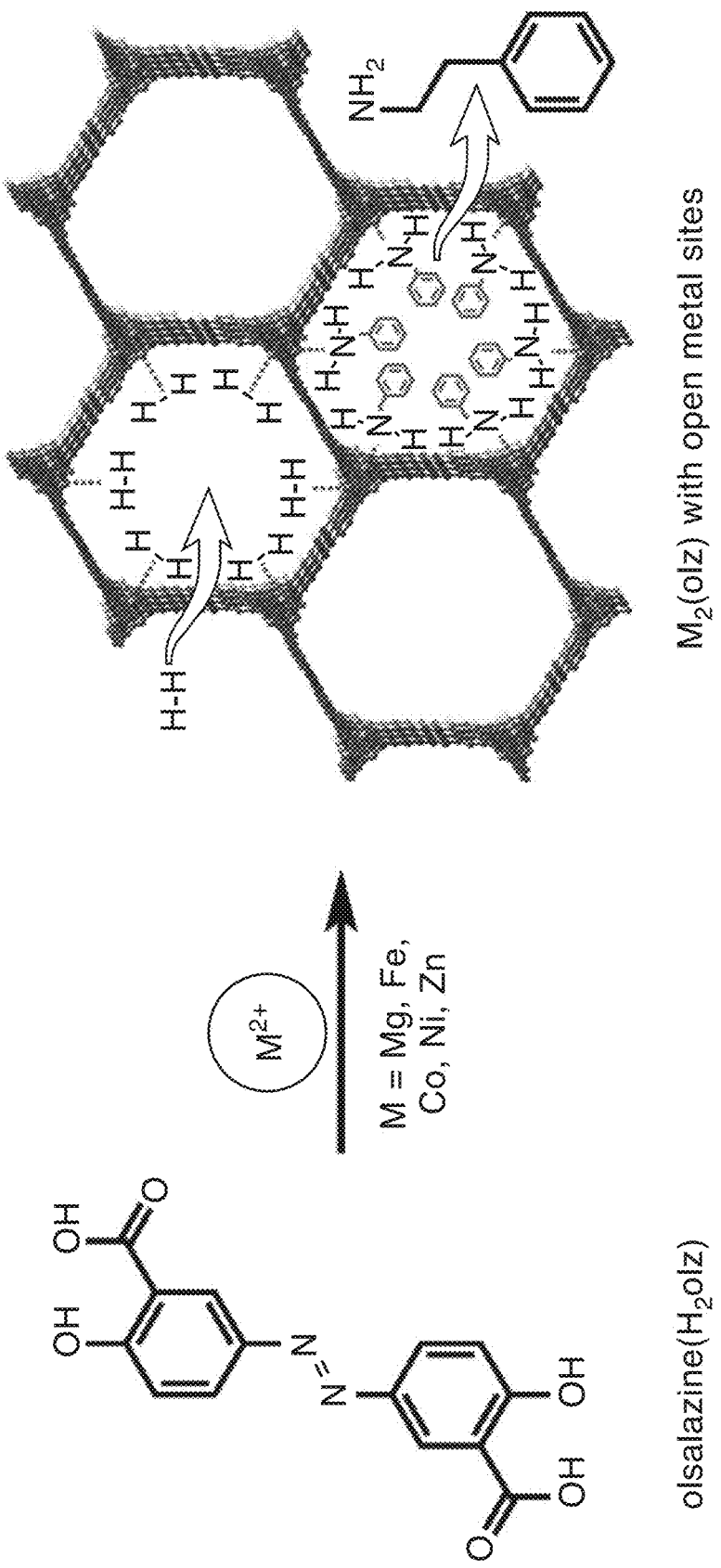
FIG. 7 is a structural model of the $M_2$(olz) framework, where M=Mg, Fe, Co, Ni, and Zn. The frameworks are synthesized using olsalazine acid ($H_4$olz) and a dication source showing gas adsorption and encapsulants disposed in pores of the framework.

The coordinated open centers of the large pore dimensions of the $M_2(olz)$ frameworks also make them good candidates for gas adsorption and storage as well as drug delivery applications. Upon activation, these materials exhibit high surface areas and contain pore apertures of approximately 27 Å with open metal sites as illustrated in FIG. 4 and FIG. 7. The open metal sites of the framework have a strong affinity for binding $H_2$ as demonstrated by $H_2$ adsorption studies and in situ IR spectroscopy. The high gravimetric capacity could be useful for other gas capture strategies that may benefit from an expanded pore size.

The as-synthesized $M_2(olz)$ frameworks were activated by performing successive solvent exchanges with DMF and methanol, followed by heating under argon and vacuum to remove residual or coordinated solvent. Surface areas of the desolvated $M_2(olz)$ frameworks were then determined from $N_2$ adsorption measurements performed at 77 K.

The $H_2$ Adsorption in each of the $M_2(olz)$ frameworks and their potential as gas storage materials was also evaluated. Hydrogen adsorption isotherms were collected at 77 K and 87 K for all activated $M_2(olz)$ frameworks, and fits to the data were obtained employing the Langmuir-Freundlich equations for dual and tri-site models. Isosteric heats of adsorption ($Q_{st}$) were calculated using the Clausius-Clapeyron relation, which revealed strong $H_2$ binding at low coverage for the Mg, Fe, Co, and Ni frameworks, with $Q_{st}$ values ranging from −10.8 to −12.1 kJ/mol. These values are comparable to those obtained for M$_2$(m-dobdc) and M$_2$(dobpdc). In the isoreticular M$_2$(dobdc) series, the removal of axial metal-bound solvent molecules results in coordinatively-unsaturated metal centers that are poised to interact with guest molecules such as CO$_2$, NO, and O$_2$. These open metal sites are also particularly selective for H$_2$ adsorption. Likewise, the presence of open metal sites in the structurally similar M$_2$(olz) frameworks was confirmed and were selective for H$_2$ adsorption indicating a good potential as an H$_2$ storage material.

As judged from the position of the inflection points in the isosteric heat plots, the performance of Co$_2$(olz) is notable because it shows near complete saturation of the metal centers. The Ni$_2$(olz) and Mg$_2$(olz) materials also exhibit reasonably good coverage at about 85% and 70% saturation, respectively. About 55% saturation is observed for Fe$_2$(olz), which may be due to the milder activation conditions employed. In the case of Zn$_2$(olz), the isosteric heat of adsorption is significantly lower in magnitude than the other frameworks in the series. This material also did not exhibit a steep rise in H$_2$ adsorption at low pressures, which suggests that open metal sites may not be present in the activated Zn$_2$(olz) material. This behavior is also consistent with the comparatively low surface area and loss in crystallinity observed upon activation.

From the description herein, it will be appreciated that that the present disclosure encompasses multiple embodiments which include, but are not limited to, the following:

1. A pharmaceutical material, comprising: (a) a metal-organic coordination polymer (M (H$_2$olz).xH$_2$O), where M=Mg, Ca, Sr, Fe, Mn, Co, Ni, Cu, Zn, or other dications and x=0 to 10; (b) wherein disassembly of the material under physiological conditions releases olsalazine.

2. The material of any preceding embodiment, wherein the coordination polymer has one-dimensional connectivity.

3. The material of any preceding embodiment, wherein the coordination polymer has two-dimensional connectivity.

4. The material of any preceding embodiment, wherein the coordination polymer has three-dimensional connectivity.

5. The material of any preceding embodiment, wherein the coordination polymer is formed with metal ions comprising combinations of two or more metal types distributed throughout the material in selected ratios.

6. A pharmaceutical material, comprising: (a) a metal-organic framework M$_2$(olz), where M=Mg, Ca, Sr, Fe, Mn, Co, Ni, Cu, Zn; (b) wherein bound or residual solvent may be replaced or removed from the pores; (c) wherein disassembly of the framework under physiological conditions releases olsalazine.

7. The material of any preceding embodiment further comprising at least one type of encapsulant disposed in pores of the framework; wherein decomposition of the framework under physiological conditions releases olsalazine and the encapsulant.

8. The material of any preceding embodiment, wherein the porous metal-organic framework is formed with metal ions comprising combinations of two or more metal types distributed throughout the framework in selected ratios.

9. The material of any preceding embodiment, wherein the encapsulant disposed in pores of the framework is grafted to an open metal site of the framework with a functional group selected from the group of an amine functional group, an alkoxide functional group, a carboxylic acid functional group, and a phenoxide functional group.

10. The material of any preceding embodiment, wherein the encapsulant disposed in pores of the framework is an encapsulant selected from the group of encapsulants consisting of a primary or a secondary amine derivative of phenethylamine.

11. A pharmaceutical material, comprising: (a) an extended coordination polymer formed from a metal and olsalazine ligand; (b) wherein the coordination polymer releases olsalazine preferentially in the lower gastrointestinal tract upon ingestion by a subject; and (c) wherein cleavage of olsalazine in the colon by bacteria results in the production of two equivalents of an anti-inflammatory 5-aminosalicylic acid (5-ASA).

12. The material of any preceding embodiment, wherein the extended coordination polymer exhibits one-dimensional connectivity (M(H$_2$olz).4H$_2$O), where M=Mg, Ca, Sr, Fe, Mn, Co, Ni, Cu, or Zn).

13. The material of any preceding embodiment, wherein the extended coordination polymer exhibits two-dimensional connectivity (M(H$_2$olz).2H$_2$O), where M=Mg, Ca, Sr, Fe, Mn, Co, Ni, Cu, or Zn).

14. The material of any preceding embodiment, wherein the extended coordination polymer exhibits three-dimensional connectivity (M(H$_2$olz)), where M=Mg, Ca, Sr, Fe, Mn, Co, Ni, Cu, or Zn.

15. The material of any preceding embodiment, wherein the extended coordination polymer exhibits three-dimensional connectivity and porosity (M$_2$(olz)), where M=Mg, Ca, Sr, Fe, Mn, Co, Ni, Cu, or Zn.

16. The material of any preceding embodiment, wherein the extended coordination polymer is comprised of combinations of two or more types of metals distributed throughout the solid in selected ratios.

17. A method for treating ulcerative colitis, the method comprising: (a) providing a therapeutic dose of an extended coordination polymer formed from a dication and olsalazine; and (b) delivering the therapeutic dose of coordination polymer to the digestive system of a patient; (c) wherein the coordination polymer releases olsalazine in the lower gastrointestinal tract of the patient; and (d) wherein cleavage of olsalazine in the colon by bacteria results in the production of two equivalents of an anti-inflammatory 5-aminosalicylic acid (5-ASA).

18. A method for treating ulcerative colitis, the method comprising: (a) providing a therapeutic dose of a porous metal-organic framework M$_2$(olz), where (M=Mg, Ca, Sr, Fe, Mn, Co, Ni, Cu, Zn, or a combination thereof) with an encapsulant disposed in pores of the framework; and (b) delivering the therapeutic dose of the framework and encapsulant to the digestive system of a patient; (c) wherein decomposition of the framework under physiological conditions releases olsalazine and the encapsulant.

19. The method of any preceding embodiment, wherein the coordination polymer is formed with metal cations comprising combinations of two or more metal types distributed throughout the material in selected ratios.

20. The method of any preceding embodiment, wherein the porous metal-organic framework is formed with metal ions comprising combinations of two or more metal types distributed throughout the framework in selected ratios.

21. The method of any preceding embodiment, wherein the encapsulant disposed in pores of the framework is grafted to an open metal site of the framework with a functional group selected from the group of an amine functional group, a thiol functional group, an alkoxide functional group, a carboxylic acid functional group, and a phenoxide functional group.

22. The method of any preceding embodiment, wherein the encapsulant disposed in pores of the framework is an encapsulant selected from the group of encapsulants consisting of phenethylamine (PEA) derivatives containing a primary or secondary amine.

23. The method of any preceding embodiment, wherein the encapsulant is selected from the group of encapsulants consisting of a drug, a bioactive compound, a macromolecule, and an imaging agent.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A pharmaceutical material, comprising:
   (a) a metalorganic coordination polymer $M_2(olz)$, where M=Mg, Ca, Fe, Co, Ni, K, Na and Zn, and olz=olsalazine;
   (b) wherein disassembly of the material under physiological conditions releases olsalazine.

2. The material of claim 1, wherein said coordination polymer has three-dimensional connectivity.

3. The material of claim 1, wherein said coordination polymer is formed with metal ions comprising combinations of two or more metals distributed throughout the material in selected ratios.

4. A pharmaceutical material, comprising:
   (a) a porous metal-organic framework $M_2(olz)$, where M=Mg, Ca, Fe, Co, Ni, K, Na and Zn and olz=olsalazine;
   (b) wherein bound or residual solvent may be replaced or removed from pores; and
   (c) wherein disassembly of the framework under physiological conditions releases olsalazine.

5. The material of claim 4, further comprising:
   at least one encapsulant disposed in pores of the framework;
   wherein decomposition of the framework under physiological conditions releases olsalazine and the encapsulant.

6. The material of claim 4, wherein said porous metal-organic framework is formed with metal ions comprising combinations of two or more metals distributed throughout the framework in selected ratios.

7. The material of claim 5, wherein said encapsulant disposed in pores of the framework is grafted to an open metal site of the framework with a functional group selected from the group of an amine functional group, an alkoxide functional group, a carboxylic acid functional group, and a phenoxide functional group.

8. The material of claim 5, wherein said encapsulant disposed in pores of the framework is an encapsulant selected from the group of encapsulants consisting of a primary or a secondary amine derivative of phenethylamine.

9. A pharmaceutical material, comprising:
   (a) an extended coordination polymer formed from an olsalazine ligand and a metal selected from the group Mg, Ca, Fe, Co, Ni, K, Na and Zn;
   (b) wherein said coordination polymer releases olsalazine in the lower gastrointestinal tract upon ingestion by a subject; and
   (c) wherein cleavage of olsalazine in the colon by bacteria results in the production of two equivalents of an anti-inflammatory 5-aminosalicylic acid (5-ASA).

10. The material of claim 9, wherein said extended coordination polymer exhibits three-dimensional connectivity $M(H_2olz)$, where M=Mg, Ca, Fe, Co, Ni, or Zn.

11. The material of claim 9, wherein said extended coordination polymer exhibits three-dimensional connectivity and porosity $M_2(olz)$, where M=Mg, Ca, Fe, Co, Ni, or Zn.

12. The material of claim 9, wherein said extended coordination polymer is comprised of combinations of two or more metals distributed throughout the polymer in selected ratios.

13. A composition, comprising:
   a porous metal-organic framework of $M_2(olz)$ where M is selected from the group of metals consisting of Mg, Ca, Fe, Co, Ni, and Zn, the framework having coordinatively unsaturated metal centers.

14. The composition of claim 13, further comprising:
   a plurality of encapsulant molecules grafted to the coordinatively-unsaturated metal sites of the framework, said molecules disposed within pores of the metal-organic framework to produce a functionalized $M_2(olz)$ framework.

15. The composition of claim 14, wherein said encapsulant molecules contain at least one Lewis-basic functional group grafted to a metal center of the framework selected from the group consisting of amines, alkoxides, phenoxides, and carboxylic acids.

16. The composition of claim 15, wherein said encapsulant molecule comprises a phenethylamine derivative selected from the group consisting of β-methylethylamine, phentermine, phenzine, amphetamine, levodopa, norepinephrine, and methyldopa.

17. The composition of claim 15, wherein said encapsulant molecule comprises a N-methylphenethylamine derivative selected from the group consisting of N-methylphenethylamine, methamphetamine, ephedrine, pseudoephedrine, phenobarbital, phenylephrine, epinephrine, isoetarine and salbutamol.

* * * * *